United States Patent [19]

Barberet et al.

[11] Patent Number: Plant 5,476

[45] Date of Patent: May 28, 1985

[54] CARNATION NAMED LONBALMA

[75] Inventors: Nicole Barberet; Yves Ducloux, both of Antibes, France

[73] Assignee: Laboratoire de Physiologie Vegetale de La Londe, Antibes, France

[21] Appl. No.: 517,232

[22] Filed: Jun. 25, 1983

[51] Int. Cl.[3] ..... A01H 5/00

[52] U.S. Cl. ..... Plt./70

[58] Field of Search ..... Plt./70

*Primary Examiner*—Robert E. Bagwill

*Attorney, Agent, or Firm*—Charles W. Rummler

[57] ABSTRACT

A new carnation cultivar particularly distinguished by the violet colored striation at the outer ends of the flower petals and a lightly pinkish background color of the petal body. These flowers are of medium size and are borne singly on long, strong stems and bloom profusely during the recurrent blooming seasons of Spring and Fall. This plant has a vigorous, upright growth habit and moderately abundant foliage.

1 Drawing Figure

BACKGROUND OF THE NEW PLANT

Our new carnation cultivar is the result of breeding efforts carried on by us at La Londe, Les Maures, France, since 1975, this new plant originating as a seedling produced from our crossing of selected and individually identified plants growing among our stock of plants maintained at La Londe for breeding purposes. This particular seedling was selected by us for propagation and test because of its very unusual flower coloration and the discovery plant was reproduced by us at La Londe, by means of cuttings. The result of that propagation effort appearing to be very favorable with respect to retention of the novel characteristics of the parent plant, we continued such propagation through several successive generations and established definitely that the novel and distinctive characteristics of the discovery plant are fully retained from generation to generation and appear to be firmly fixed.

DESCRIPTION OF THE DRAWING

Our new carnation variety is illustrated by the accompanying photographic drawing which shows, in full color, a typical arrangement of buds and flowers in various stages of opening, the colors shown being as nearly true to those specified herein as is reasonably possible to obtain by conventional photographic procedures.

DESCRIPTION OF THE NEW PLANT

The following is a detailed description of our new carnation discovery based upon observations of greenhouse grown plants made at La Londe, France, in the Spring of 1983, the color designations being specified according to The R. H. S. Colour Chart published by The Royal Horticultural Society of London, England.

THE PLANT

Origin: Seedling.
Parentage:
- *Seed parent.*—Stock Plant No. 9 C 8 (unpatented).
- *Pollen parent.*—Stock Plant No. 7 R 3 (unpatented).

Classification:
- *Botanic.*—*Dianthus Caryophyllus.*
- *Commercial.*—Standard Carnation.

Form: Tall, erect bush with at least four stems being emitted near the ground.
Height: Average; about 120 cm. at eight months.
Main stem:
- *Length.*—Less than 15 cm. due to pinching.

Branching character: Rather few branches.
Growth habit: Vigorous, upright and rigid.
Foliage:
- *Quantity.*—Moderately abundant.
- *Number of leaves.*—More than 120.
- *Leaf size.*—Average of about 15 cm. long and 1.2 cm. wide at the seventh node.
- *Leaf shape.*—Linear with curved margins.
- *Texture.*—Leathery.
- *Color.*—Upper side — 189A. Under side — 189A.
- *Ribs and veins.*—Hardly noticeable.
- *Rachis.*—Hardly noticeable.

THE BUD

Form: Ovoid.
Size:
- *Diameter.*—Averages about 2.3 cm.
- *Length.*—Averages about 3.7 cm.

Rate of opening: Normal for carnations.
Color of petals:
- *When sepals first divide.*—Light pink but less than the body color in full bloom.
- *When petals begin to unfurl.*—Less pinkish than in full bloom.

Sepals:
- *Number.*—Five to six.
- *Shape.*—Joined at lower part, the upper part being of acute character with a sharp pointed tip. The sepals are hooded over the bud and continue to stand up when the flowers open.
- *Color.*—Inside — Greenish white. Outside — 143C and 144C.
- *Striae.*—Longitudinal.

Calyx:
- *Size.*—Medium.
- *Shape.*—Bell-shaped.
- *Splitting.*—The calyx very rarely splits.
- *Aspect.*—Glandular.

Flower stem:
- *Length.*—About 73 cm.
- *Character.*—Rigid and erect.
- *Color.*—189A.

THE FLOWER

Blooming habit: Recurrent and profuse during the mid-season of Spring and Fall.

Size of bloom: Medium.

*Diameter.*—Averages about 9.1 cm.

*Depth.*—Averages about 6 cm.

Borne: Singly.

Shape:

*When bloom first opens.*—High centered.

*When bloom matures.*—Ball-shaped.

Petalage:

*Number of petals.*—Averages about 72.

*Arrangement.*—Imbricated.

*Form.*—Fan-shaped with serrated outer margin.

*Texture.*—Soft.

*Appearance.*—Satiny.

*Color.*—Outer Petal — 56C and 61A variations. Base — Greenish white. Reverse side — 56D and 60C. Inside Petal — About the same as the outer petals.

Flower stem:

*Length.*—About 73 cm.

*Color.*—189A.

*Character.*—Upright and with good strength.

Fragrance: Light fragrance is present.

Persistence: The petals hang on and dry.

Lasting quality:

*As cut flower.*—At least ten days with vase keeping.

REPRODUCTIVE ORGANS

Stamens:

*Number.*—15 To 23.

*Arrangement.*—Around the pistils.

*Anthers.*—Size: Less than 4 mm. Color: Whitish.

*Filaments.*—Color: Whitish.

Pistils:

*Number.*—Occasionally three.

*Styles.*—Color — White.

*Stigmas.*—Color —Lightly violet. The stigmas have papillas and crests.

Character of ovaries: The ovary is lightly ribbed.

The violet colored striation against a lightly pinkish background is a particularly distinctive character of the flowers of this new variety. The calyx of this flower almost never splits and its stem is somewhat thicker than that found in similar carnation varieties.

We claim:

1. A new and distinctive carnation cultivar, substantially as herein shown and described, characterized by the generally violet colored striation on the lightly pinkish background of the many petals of its medium sized blooms.

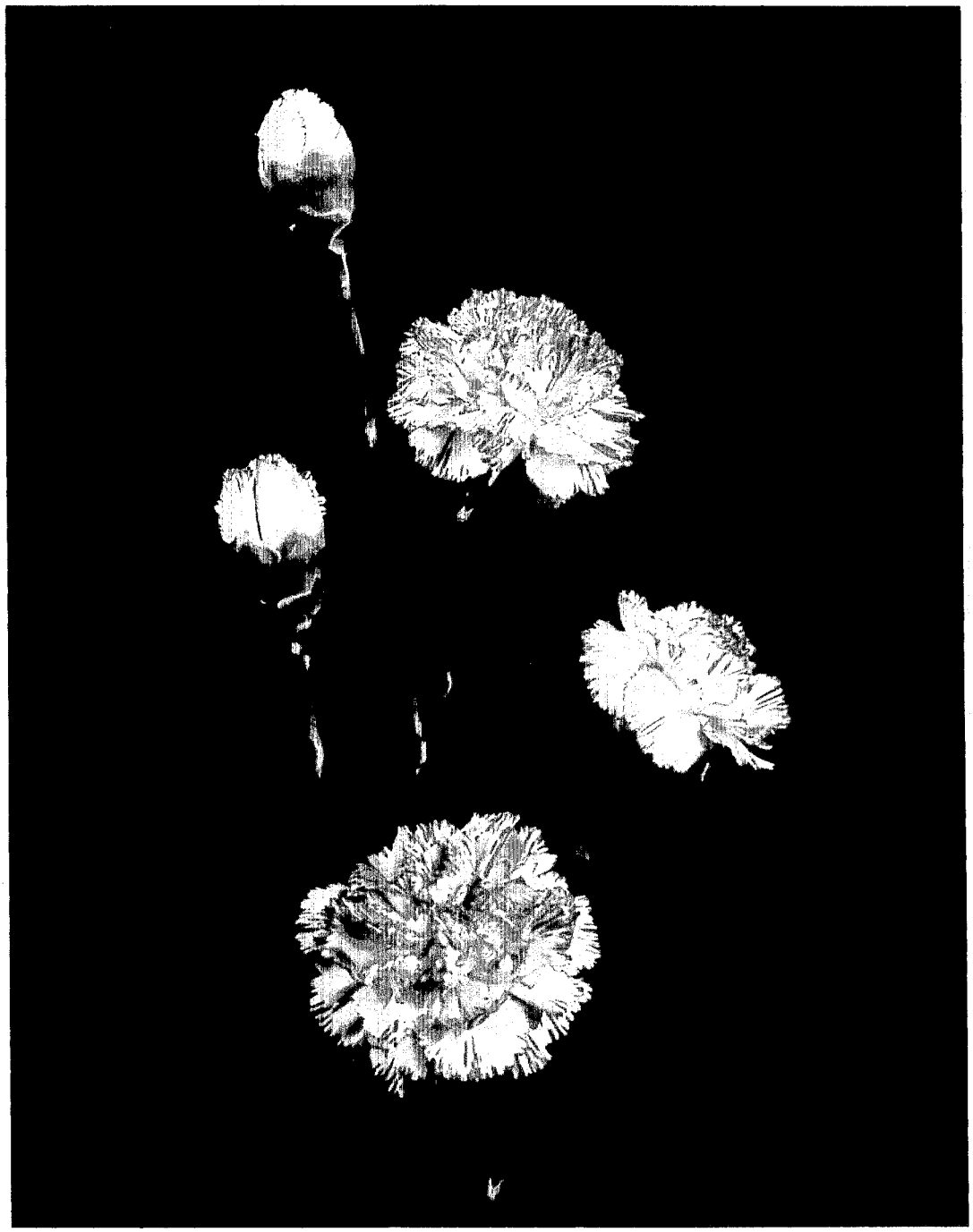

* * * * *